US009797806B1

(12) United States Patent
Zhou et al.

(10) Patent No.: US 9,797,806 B1
(45) Date of Patent: Oct. 24, 2017

(54) PC/APC DUAL-PURPOSE ADAPTER FOR INSPECTING CIRCULAR RUGGEDIZED FIBER OPTIC CONNECTORS

(71) Applicant: LIGHTEL TECHNOLOGIES, INC., Renton, WA (US)

(72) Inventors: Ge Zhou, Renton, WA (US); Theodore E. Bartunek, Kent, WA (US)

(73) Assignee: LIGHTEL TECHNOLOGIES, INC., Renton, WA (US)

( * ) Notice: Subject to any disclaimer, the term of this patent is extended or adjusted under 35 U.S.C. 154(b) by 0 days.

(21) Appl. No.: 15/448,515

(22) Filed: Mar. 2, 2017

(51) Int. Cl.
| G01M 11/00 | (2006.01) |
| G01N 21/952 | (2006.01) |
| G02B 6/38 | (2006.01) |
| G01N 21/95 | (2006.01) |

(52) U.S. Cl.
CPC ........... *G01M 11/30* (2013.01); *G01N 21/952* (2013.01); *G02B 6/385* (2013.01); *G02B 6/3807* (2013.01); *G02B 6/3825* (2013.01); *G02B 6/3882* (2013.01); *G02B 6/3893* (2013.01); *G01N 2021/9511* (2013.01)

(58) Field of Classification Search
CPC ...... G01M 11/30; G01M 11/31; G01M 11/33; G01N 21/88; G01N 21/8803; G01N 21/896; G01N 21/952; G01N 2021/9511
USPC .......................... 356/73.1; 385/53, 88, 89, 90
See application file for complete search history.

(56) References Cited

U.S. PATENT DOCUMENTS

| 5,748,818 | A  * | 5/1998 | Weiss | ................... | G02B 6/3831 |
| | | | | | 385/59 |
| 6,461,055 | B1 * | 10/2002 | Zimmel | ................. | G02B 6/266 |
| | | | | | 385/140 |
| 7,336,884 | B2 * | 2/2008 | Zhou | .................... | G02B 6/3833 |
| | | | | | 359/368 |
| 8,104,976 | B2 * | 1/2012 | Zhou | .................... | G02B 6/3833 |
| | | | | | 359/368 |
| 8,976,345 | B2 * | 3/2015 | Zhou | ..................... | G01M 11/30 |
| | | | | | 356/73.1 |
| 9,110,252 | B2 * | 8/2015 | Zhou | .................... | G02B 6/3866 |
| 2006/0204178 | A1 * | 9/2006 | Theuerkorn | ......... | G02B 6/3821 |
| | | | | | 385/59 |
| 2015/0177469 | A1 * | 6/2015 | Nadeau | ............. | G01M 11/3154 |
| | | | | | 356/73.1 |
| 2016/0170151 | A1 * | 6/2016 | Baribault | ............... | G02B 6/385 |
| | | | | | 356/73.1 |

(Continued)

*Primary Examiner* — Gordon J Stock, Jr.
(74) *Attorney, Agent, or Firm* — Pai Patent & Trademark Law Firm; Chao-Chang David Pai

(57) ABSTRACT

The dual-purpose adapter for inspecting circular (plug-type or receptacle-type) ruggedized fiber optic connector has a guide and a fitting tip. The guide is formed by fastening a template inserter to a frame in two alternative opposite directions. The template inserter has light channels corresponding in relative positions to the endfaces in the ruggedized connector, and two locating holes for coupling and aligning with the ruggedized connector through two guide pins. Depending upon the direction in which the template inserter is fastened to the frame, the fitting tip may be inserted into a respective end of the light channels to allow the optical axis of an inspector probe connected to it to intersect at right angle with PC or APC endfaces for inspection by the inspector probe. For receptacle-type connectors, the guide further includes the two guide pins which can be locked from axial movement at two positions.

13 Claims, 11 Drawing Sheets

(56) References Cited

U.S. PATENT DOCUMENTS

2016/0341904 A1* 11/2016 Morin-Drouin ....... G02B 6/385

* cited by examiner

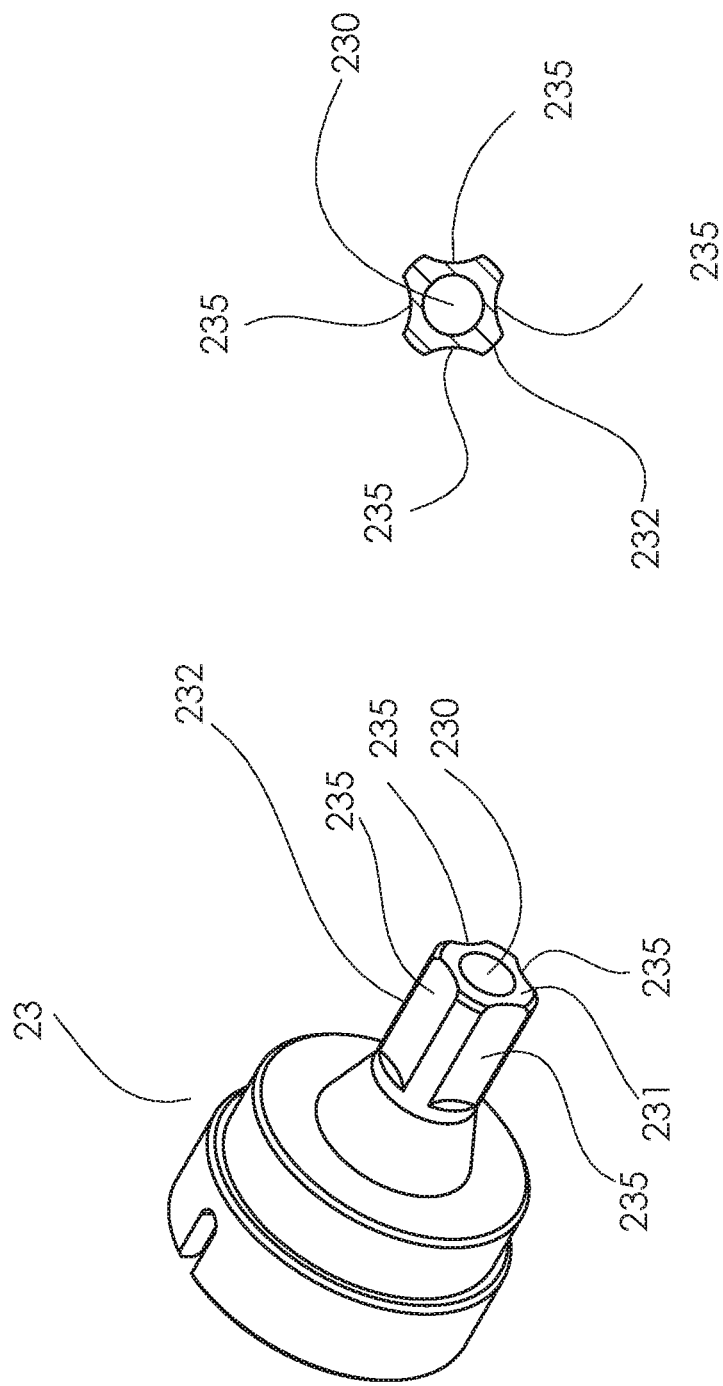

PC/APC DUAL-PURPOSE ADAPTER FOR INSPECTING CIRCULAR RUGGEDIZED FIBER OPTIC CONNECTORS

BACKGROUND OF THE INVENTION

1. Field of the Invention

The invention relates to fiber optic connector inspection and more particularly to a dual-purpose adapter for inspecting circular ruggedized fiber optic connectors using an inspector probe. The dual-purpose adapter according to this invention may be connected to an inspector probe in two opposite directions, one for inspecting Physical Contact ("PC") connector endfaces and the other for inspecting Angled Physical Contact ("APC") connector endfaces embedded in the circular ruggedized fiber optic connector.

2. Description of the Related Art

Robust fiber optic interconnects are needed in harsh environments. For example, military and aerospace systems must perform in hostile climates, inclement weather and adverse surroundings. Similarly, geophysical applications, emergency deployable communication systems, broadcasting, and security applications, etc. subject interconnects to demanding conditions. As a result, various kinds of so-called ruggedized fiber optic connectors capable to perform in harsh environments and demanding conditions have been developed and applied.

Two common types of ruggedized fiber optic connectors are the plug-type and the receptacle-type. A plug-type ruggedized connector 30 is shown in FIG. 1 and FIG. 2, and a receptacle-type ruggedized connector 50 is shown in FIG. 10. In either the plug-type ruggedized connector 30 or the receptacle-type ruggedized connector 50, a plurality of fiber optic termini 330 extend through the rear side of the ruggedized connector 30/50 and are fixedly held in a circular cylindrical holding block 32/52; each of the fiber optic termini 330 has a fiber optic endface 331 exposed in an open chamber 320/520 surrounded by an outer shell 310/510 and facing the front side of the respective ruggedized connector 30/50. In most cases, the fiber optic endface 331 is either a PC endface 3311 (as shown in FIG. 6) or an APC endface 3312 (as shown in FIG. 7). The PC endface is perpendicular to the axis of the fiber optic terminus 330, whereas the APC endface is tilted from the perpendicular plane (i.e. a plane that is perpendicular to the axis of the fiber optic terminus 330) by an angle α, which will be referred to as the "tilted angle" in the following. The tilted angle of APC endfaces is almost always 8°. The fiber optic endfaces 331 of the fiber optic termini 330 are arranged in a certain regular pattern, usually symmetrically or equiangularly (relative to the center of the holding block 32/52, depending upon the particular connector models and applications.

In the plug-type ruggedized connector 30, two diametrically placed guide pins 340 protrude forward from the holding block 32 into the open chamber 320. The guide pins 340 are intended for proper alignment and contact of the fiber optic termini 330 with the termini of another matching ruggedized connector (not shown). In contrast, in the receptacle-type ruggedized connector 50, no guide pins are equipped; instead, two diametrically placed locating holes 521 are formed in the holding block 52 for proper alignment and contact with termini of another matching ruggedized connector (not shown).

FIG. 1 and FIG. 2 illustrate a conventional adapter 7 for inspecting the plug-type ruggedized connector 30 with PC endfaces 3311 using an inspector probe 10. The conventional adapter 7 comprises a guide 70 and a fitting tip 73. As shown in FIG. 1, the guide 70 has two locating holes 729 corresponding to the two guide pins 340 of the plug-type ruggedized connector 30, and a plurality of light channels 720 corresponding (in number and relative positions) to the plurality of PC endfaces 3311 embedded in the plug-type ruggedized connector 30. When the guide 70 is coupled with the front end 314 of the plug-type ruggedized connector 30 by inserting the front portion 710 of the guide 70 into the open chamber 320 of the plug-type ruggedized connector 30 and mating the two locating holes 729 with the two guide pins 340, the front annular surface 713 of the guide 70 will be stopped at the front end 314 of the plug-type ruggedized connector 30 and the plurality of light channels 720 will correspond in relative position to the plurality of the PC endfaces 3311, respectively. Namely, each PC endface 3311 will be placed in the middle of one respective light channel 720 when viewed from the rear side of the guide 70. When the fitting tip 73 is fitted on the front end 101 of the inspector probe 10, the optical axis 100 of the inspector probe 10 will be collinear with the central axis 730 of the fitting tip 73. The fitting tip 73 has a front stem 732 which can be fittingly inserted into each of the light channels 720 of the guide 70 through the rear section 722 until the front end surface 731 of the fitting tip 73 comes in contact with an inner end surface 7221 of the rear section 722. After the guide 70 is coupled with the plug-type ruggedized connector 30, the fitting tip 73 is inserted into one of the light channels 720 of the guide 70, and the fitting tip 73 is connected with the front end 101 of the inspector probe 10, the endface 331 that is in view through the light channel 720 into which the fitting tip 73 is inserted may be inspected by the inspector probe 10. By repeating these steps, all the PC endfaces 3311 of the plug-type ruggedized connector 30 may be inspected one by one.

However, no conventional adapters have been made available for inspecting the plug-type ruggedized fiber optic connectors with APC endfaces 3312 using the inspector probe 10, nor are there any conventional adapters for inspecting receptacle-type ruggedized fiber optic connectors 50 with PC endfaces 3311 or APC endfaces 3312. Granted that specialized adapters may be designed for the APC endfaces and for the receptacle-type ruggedized connectors 50, it would be very cumbersome and costly to keep all the different adapters around for all the connector inspection tasks.

Therefore, a simple, compact, and multi-purpose adapter that enables an inspector probe 10 to inspect both types of ruggedized connectors, and for both PC and APC endfaces, will be very convenient and useful to carry out the inspection tasks, considering the critical importance of ruggedized connectors in the broad range of applications.

BRIEF SUMMARY OF THE INVENTION

The object of the present application is to provide a PC/APC dual-purpose adapter for inspecting a circular ruggedized fiber optic connector having PC or APC endfaces. The dual-purpose adapter can be easily and quickly switched between two operating modes, one for inspecting PC endfaces and the other for inspecting APC endfaces. Moreover, the dual-purpose adapter of the present application for inspecting the plug-type ruggedized connector can be used for inspecting the receptacle-type ruggedized connector with a simple design modification and additional parts.

The PC/APC dual-purpose adapter for inspecting the plug-type ruggedized connector according to the present application includes a frame, a template inserter, and a fitting tip. The template inserter comprises a first end surface, a second end surface parallel to the first end surface, a cylindrical outer surface between the first end surface and the second end surface. The template inserter further includes a plurality of internal light channels extending between the first end surface and the second end surface and two locating holes perpendicularly extending between the first end surface and the second end surface. In addition, the template inserter has a first male screw thread and a second male screw thread formed on the outer surface.

The plurality of light channels of the template inserter are so arranged as to respectively correspond to a plurality of endfaces in the plug-type ruggedized connector. Furthermore, each of the internal light channels comprises a cylindrical first end section, a cylindrical second end section, and a mid section between the first end section and the second end section; the first end section is perpendicular to the first end surface, whereas the second end section is tilted at an angle $\alpha$ from a normal of the second end surface, wherein $\alpha$ is the tilted angle of APC endfaces of the ruggedized connector, normally 8°.

The frame has a front annular connecting portion for coupling with the plug-type ruggedized connector, and an internal cylindrical surface having thereon a female screw thread matching the first and the second male screw threads of the template inserter. Therefore, the frame may be connected to the template inserter either through the first male screw thread with the first end surface (and therefore the first end sections of the light channels) facing the frame, or through the second male screw thread with the second surface (and therefore the second end sections of the light channels) facing the frame.

When inspecting the plug-type ruggedized connector with PC endfaces, the template inserter is connected with the frame with the first male screw thread, the fitting tip is inserted into the first end section of a selected internal light channel, the frame is coupled with the plug-type ruggedized connector, and two guide pins of the plug-type ruggedized connector are respectively inserted into the two locating holes of the template inserter, then a PC endface of the plug-type ruggedized connector will be in view through the selected internal light channel for inspection by the inspector probe connected to the fitting tip.

Similarly, when inspecting the plug-type ruggedized fiber optic connector with APC endfaces, the template inserter is fastened to the frame with the second male screw thread, the fitting tip is inserted into the second end section of a selected internal light channel, then an APC endface of the plug-type ruggedized fiber optic connector will be in view through the selected internal light channel for inspection by the inspector probe connected to the fitting tip.

The PC/APC dual-purpose adapter for inspecting the receptacle-type ruggedized connector according to the present application is similar to the dual-purpose adapter described above for inspecting the plug-type ruggedized connector, except that the former further includes two guide pins received in the locating holes of the template inserter and a mechanism for locking/unlocking the two guide pins with respect to axial movement in the locating holes. In the illustrative embodiment of the present invention, the guide pins may be locked at two locking positions. At the first locking position, the guide pins protrude out of the second end surface of the template inserter to be respectively received in two locating holes of the receptacle-type ruggedized connector. At the second locking position, the guide pins protrude out of the first end surface of the template inserter to be respectively received in two locating holes of the receptacle-type ruggedized connector. The PC or APC endfaces can then be inspected in the same manner as described above for the plug-type ruggedized connector.

To accommodate the angled second end section of the light channels of the template inserter, the front stem of the fitting tip is shaped to have a plurality of, preferably four, grooves that are evenly distributed around the outer surface of the front stem.

BRIEF DESCRIPTION OF THE DRAWINGS

The following detailed description of the preferred embodiments of the PC/APC dual-purpose adapter according to the present invention can best be understood when read in conjunction with the following drawings, in which:

FIG. 14 is a front perspective view of the fitting tip for the PC/APC dual-purpose adapter according to the present application.

FIG. 15 shows the cross-section of the front stem of the fitting tip for the PC/APC dual-purpose adapter according to the present application.

DETAILED DESCRIPTION OF THE INVENTION

Hereafter, examples will be provided to illustrate the preferred embodiments of the PC/APC dual-purpose adapter for inspecting circular ruggedized fiber optic connectors according to the present invention. The structure and components of the PC/APC dual-purpose adapter and its operations and advantages will become more apparent from the following description of the embodiments of the present invention in conjunction with the accompanying drawings.

In the following, the PC/APC dual purpose adapter of the present application will be described for both the plug-type ruggedized connector 30 and the receptacle-type ruggedized connector 50.

PC/APC Dual-Purpose Adapter for Circular Plug-Type Ruggedized Connector

Figure 3:
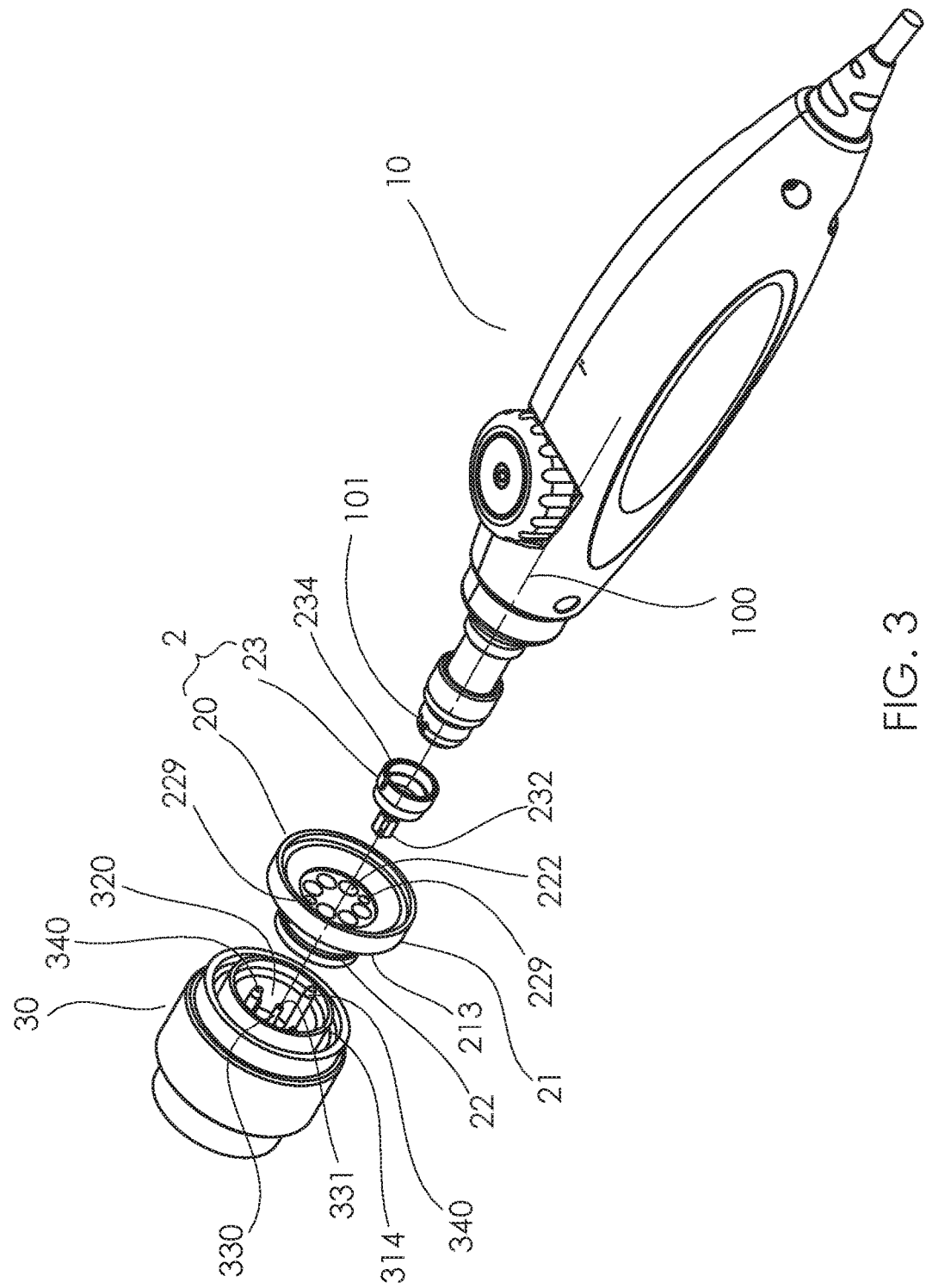
FIG. 3 shows how a PC/APC dual-purpose adapter (including a guide and a detached fitting tip) according to the present application is connected between a plug-type ruggedized connector and an inspector probe for inspecting fiber optic endfaces in the ruggedized connector.
Figure 4:
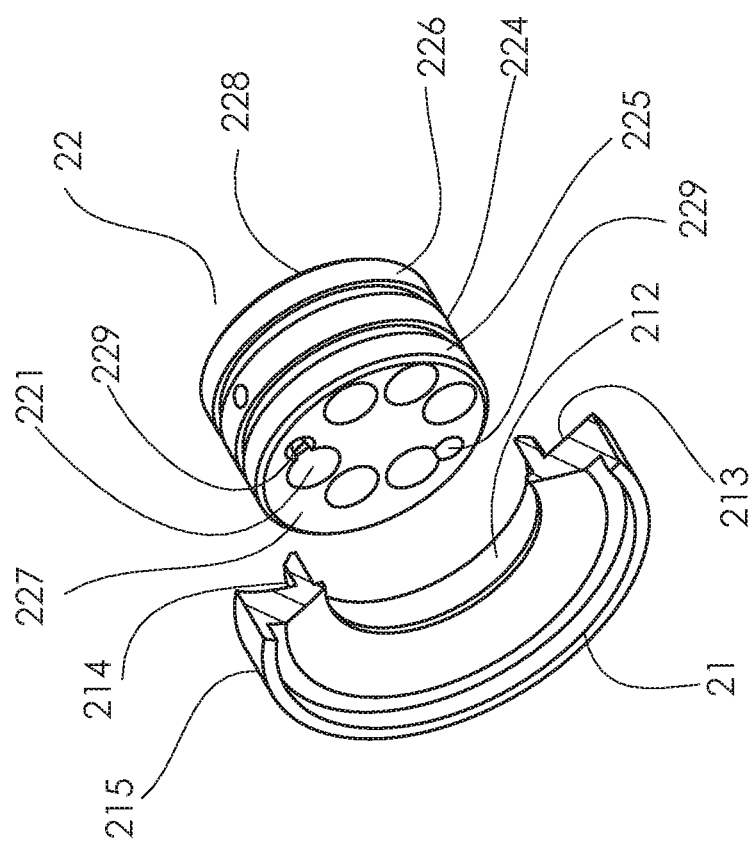
FIG. 4 shows how the template inserter and the frame are coupled to form the guide of the present application for inspecting PC endfaces in the plug-type ruggedized connector.
Figure 5:
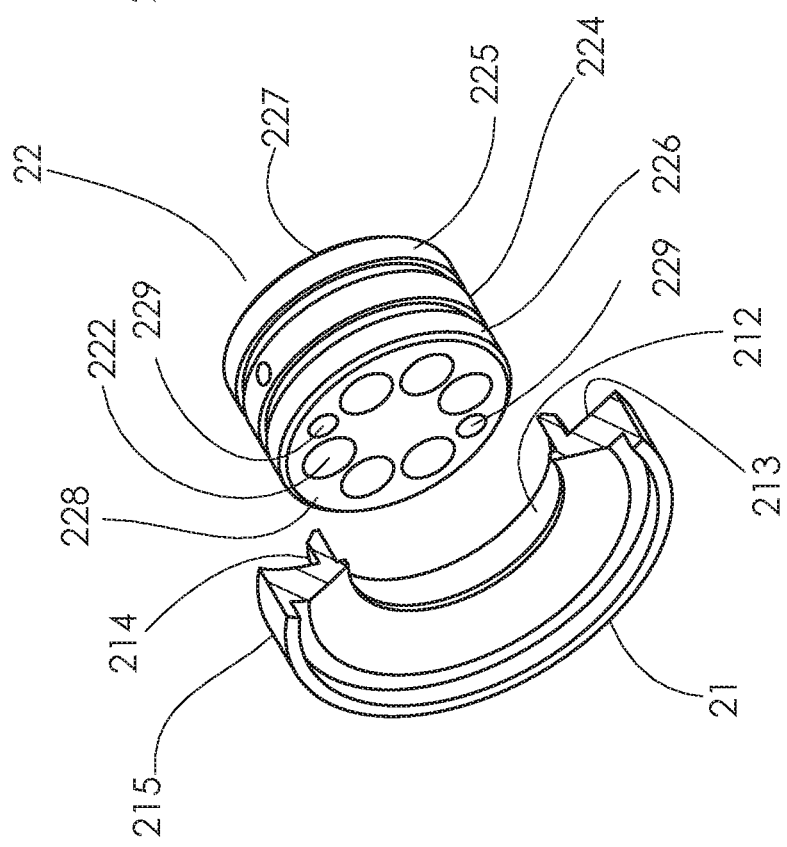
FIG. 5 shows how the template inserter and the frame are coupled to form the guide of the present application for inspecting APC endfaces in the plug-type ruggedized connector.

FIGS. 3-5 show a PC/APC dual-purpose adapter 2 for a circular plug-type ruggedized connector 30 according to the present application. The PC/APC dual-purpose adapter 2 includes a guide 20 and a fitting tip 23, and the guide 20 includes a template inserter 22 and a frame 21. In FIG. 3, the PC/APC dual-purpose adapter 2 is placed between a plug-type ruggedized connector 30 and an inspector probe 10, ready to be connected for inspecting the fiber optic endfaces 331 in the plug-type ruggedized connector 30. Essentially, the template inserter 22 may be coupled with the frame 21 in two opposite directions, as shown in FIG. 4 and FIG. 5, for inspecting PC endfaces 3311 and APC endfaces 3312, respectively. The front connecting portion 214 of the frame 21 and the template inserter 22 are configured to fittingly couple with a front portion of the plug-type ruggedized connector 30. When the frame 21 and the template inserter 22 are coupled with the plug-type ruggedized connector 30, and the fitting tip 23 is connected between the template inserter 22 and the inspector probe 10, the fiber optic endfaces 331 enclosed in the plug-type ruggedized connector 30 may be inspected one by one by the inspector probe 10.

Figure 1:
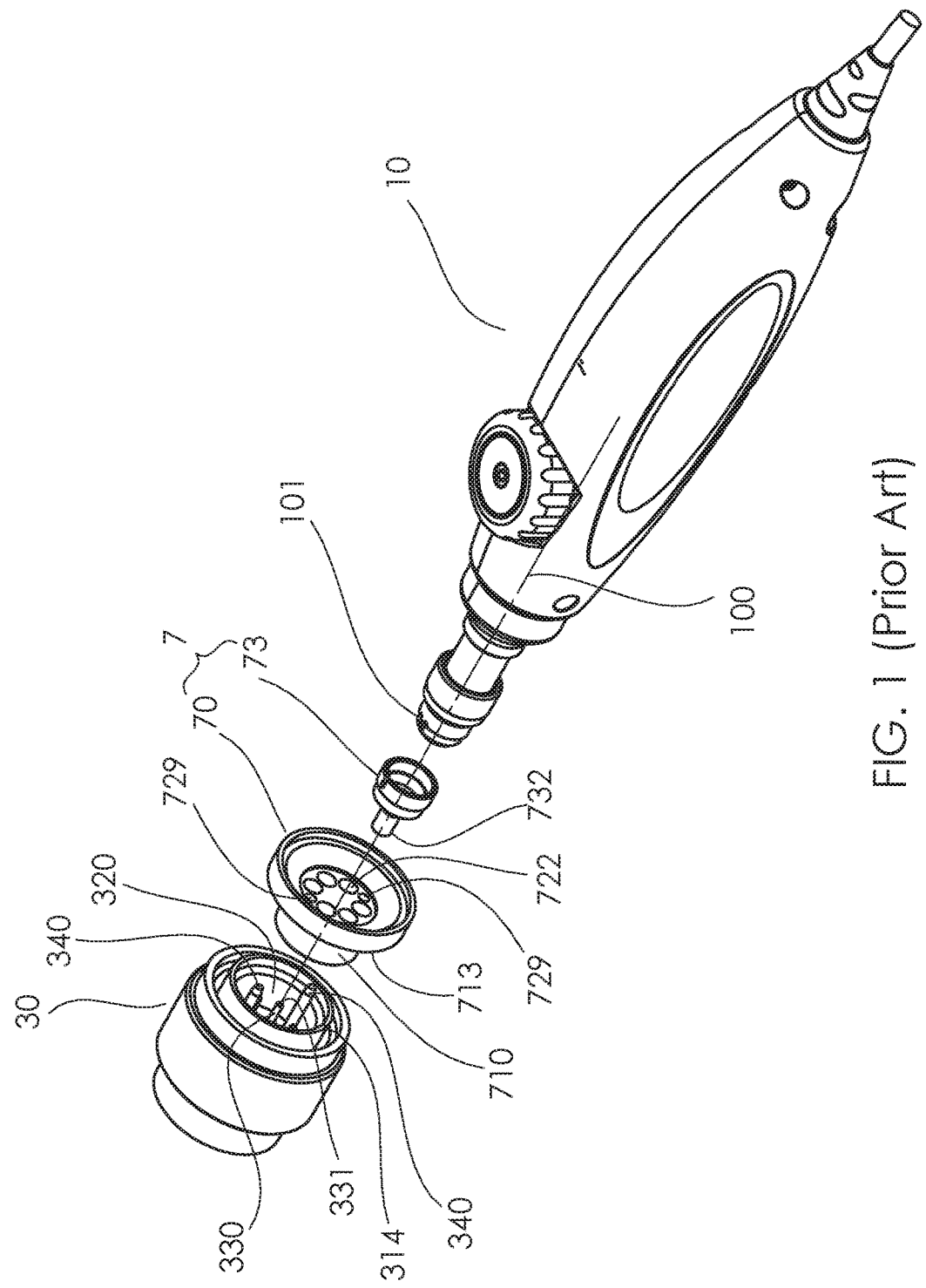
FIG. 1 shows how a conventional adapter (including a guide and a detached fitting tip) is connected between a plug-type ruggedized connector and an inspector probe for inspecting the fiber optic endfaces in the ruggedized connector.
Figure 2:
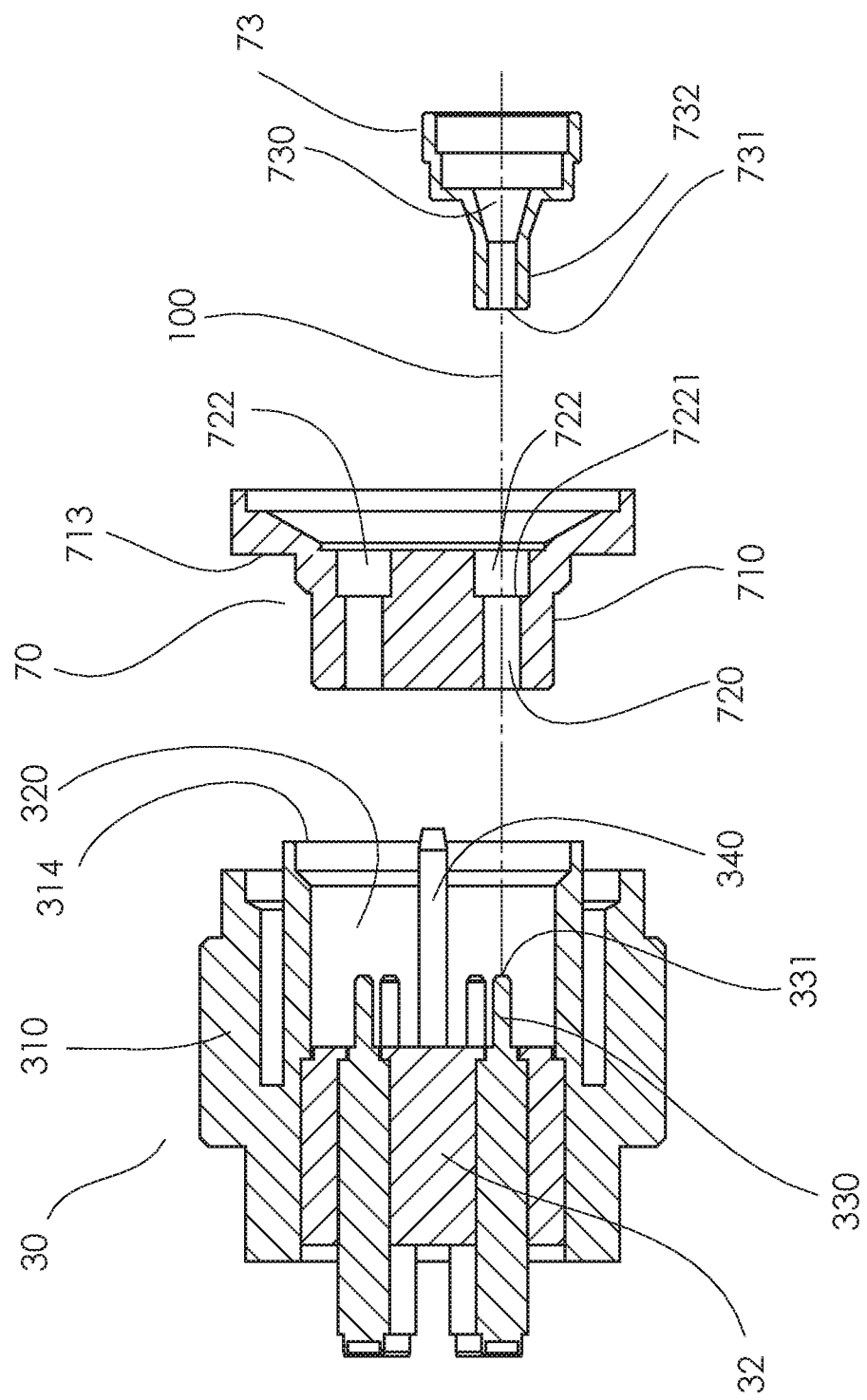
FIG. 2 is an exploded sectional view showing how the conventional adapter is coupled with the plug-type ruggedized connector for inspecting PC endfaces enclosed therein.

The front stem 232 of the fitting tip 23 is configured for inserting into the template inserter 22 and the rear portion 234 of the fitting tip 23 is configured for fitting on the front end 101 of a conventional inspector probe 10. The fitting tip 23 is similar to a conventional fitting tip 73 shown in FIG. 1, except that the front stem 232 of the fitting tip 23 may have a different outer contour from the front stem 732 of the conventional fitting tip 73 to accommodate its connection with the template inserter 22 for inspecting APC endfaces 3312. This aspect will be explained later. Similar to the conventional fitting tip 73, when the fitting tip 23 is fitted on the front end 101 of an inspector probe 10, the central axis 230 of the fitting tip 23 will be collinear with the optical axis 100 of the inspector probe 10.

Figure 6:
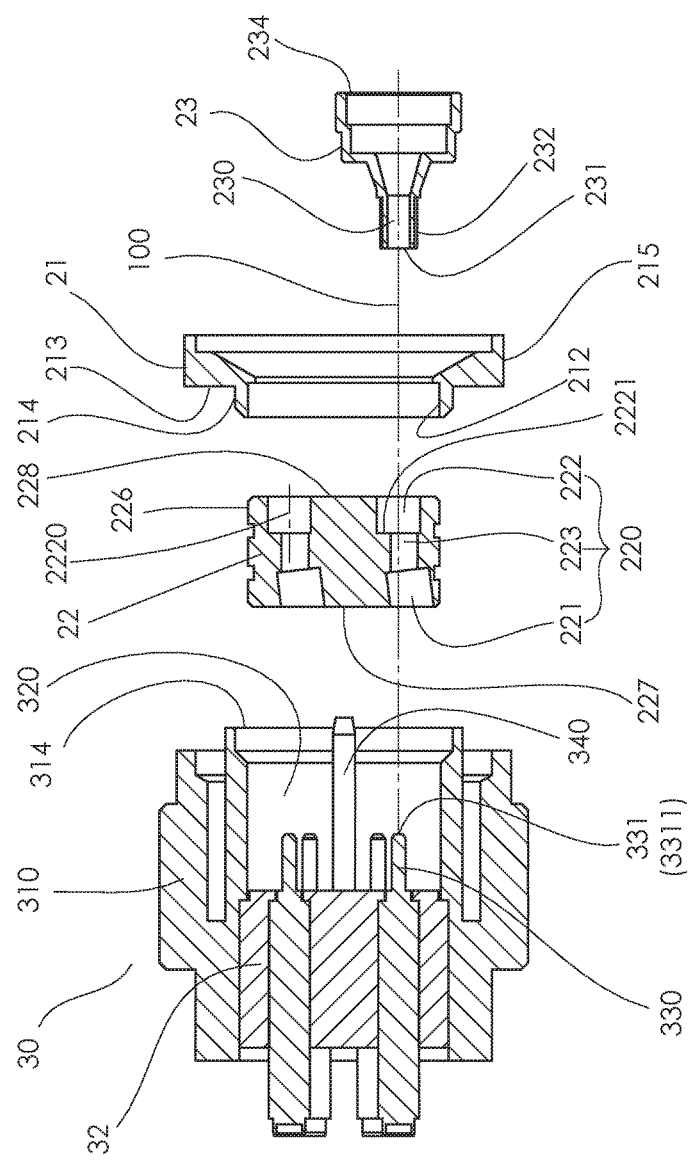
FIG. 6 is an exploded sectional view showing how the PC/APC dual-purpose adapter of the present application is connected together with the plug-type ruggedized connector for inspecting PC endfaces enclosed therein.
Figure 7:
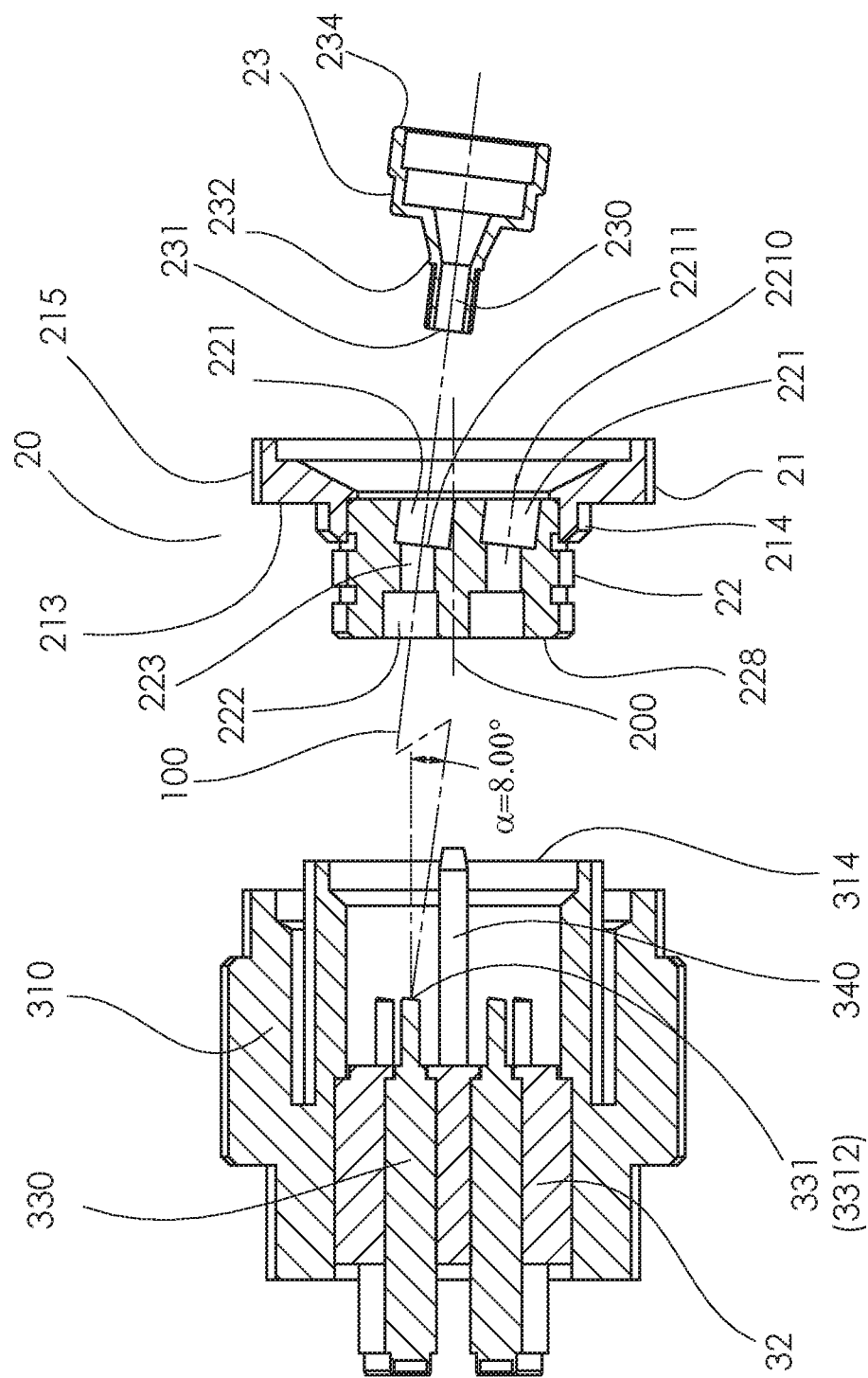
FIG. 7 is an exploded sectional view showing how the PC/APC dual-purpose adapter of the present application is connected together with the plug-type ruggedized connector for inspecting APC endfaces enclosed therein.

As shown in FIG. 4 and FIG. 5, the guide 20 comprises a template inserter 22 and a frame 21 connectable with the template inserter 22. The frame 21 has a double annular structure with a front annular connecting portion 214 and a rear annular portion 215. The frame 21 has an inner circular cylindrical surface, on which a female screw thread 212 is formed for fastening to either of two matching male screw threads 225, 226 of the template inserter 22. The outer surface of the front annular connecting portion 214 is configured to be fittingly received in the open chamber 320 of the plug-type ruggedized connector 30. The rear annular portion 215 has an outer diameter greater than that of the front annular connecting portion 214, thus forming an annular front surface 213, which will be stopped at the front end 314 of the plug-type ruggedized connector 30 when the front annular connecting portion 214 has been properly received in the open chamber 320 of the plug-type ruggedized connector 30. Furthermore, the rear annular portion 215 has an inner diameter proportionally increasing in the direction towards the rear end of the frame 21, thus forming an expanding opening facing the rear side of the frame. As shown in FIG. 6 and FIG. 7, the rear-facing expanding opening of the rear annular portion 215 of the frame 21 is provided to accommodate the shape of the fitting tip 23 inserted into the template inserter 22.

Referring again to FIGS. 4-7, the template inserter 22 is a generally cylindrical body having a first end surface 228, a second end surface 227 parallel to the first end surface 228, a plurality of light channels 220 extending between the first end surface 228 and the second end surface 227, and two locating holes 229 perpendicularly extending between the first end surface 228 and the second end surface 227.

In order to couple the template inserter 22 with the frame 21 to form a guide 20, a first male screw thread 226 and a second male screw thread 225, both matching the female screw thread 212 of the frame 21, are provided on the outer surface 224 of the template inserter 22. Therefore, the template inserter 22 can be fastened to the frame 21 in either of two opposite directions, i.e. with the first male screw thread 226 fastened to the female screw thread 212 of the frame 21 or with the second male screw thread 225 fastened to the female screw thread 212 of the frame 21. In this embodiment, the first male screw thread 226 is adjacent to the first end surface 228 and the second male screw thread 225 is adjacent to the second end surface 227. Therefore, when the template inserter 22 is fastened to the female screw thread 212 of the frame 21 via the first male screw thread 226, the first end surface 228 will face the rear side of the frame 21. Conversely, when the template inserter 22 is fastened to the female screw thread 212 of the frame 21 via the second male screw thread 225, the second end surface 227 will face the rear side of the frame 21. However, the design of the frame 21 and the template inserter 22 may be altered to cause each end surface to face the rear side of the frame 21 by fastening the male screw thread more adjacent to the other end surface to the female screw thread 212.

The two locating holes 229 are diametrically disposed in the template inserter 22 for fittingly receiving the two guide pins 340 of the plug-type ruggedized connector 30 to be inspected. Each of the locating holes 229 has a diameter essentially the same as the diameter of the guide pins 340 of the plug-type ruggedized connector 30. The plurality of light channels 220 corresponds in number and relative positions to the plurality of fiber optic endfaces 331 enclosed in the plug-type ruggedized connector 30. The template inserter 22 is configured such that when the frame 21 is coupled with the front end 314 of the plug-type ruggedized connector 30 with the two guide pins 340 inserted through either one of the end surfaces 228/227 into the locating holes 229 of the template inserter 22 already coupled with the frame 21, each of the fiber optic endfaces 331 in the plug-type ruggedized connector 30 will be in view through a respective one of the light channels 220. Thus, a light path is formed from the fiber optic endfaces 331, through the respective light channel 220 and out of the other end surface 227/228.

Each of the light channels 220 comprises a cylindrical first end section 222 perpendicularly extending inwards from the first end surface 228, a cylindrical second end section 221 extending inwards from the second end surface 227 at an angle α (which is the tilted angle characteristic of the APC endfaces to be inspected) relative to a normal of the second end surface 227, and a mid section 223 between the first end section 222 and the second end section 221. The angle α is set to be the angle at which the APC endfaces of the plug-type ruggedized connector 30 are tilted (from a plane perpendicular to the axis of the corresponding optical fiber), The tilted angle α characteristic of most APC endfaces 3312 these days is 8°. Both the first end section 222 and the second end section 221 of each light channel 220 have an inner surface for fittingly receiving and holding the front stem 232 of the fitting tip 23. In other words, the inner surface of the first end section 222 and the second end section 221 are cylindrical with circular cross sections and corresponding to the outer surface of the front stem 232 of the fitting tip 23. Therefore, as shown in FIG. 6, when the front stem 232 of the fitting tip 23 is inserted into the first end section 222 of a light channel 220, the central axis 230 of the fitting tip 23 (and therefore the optical axis 100 of the inspector probe 10 fitted with the fitting tip 23) will be collinear with the central axis 2220 of the first end section 222. Conversely, as shown in FIG. 7, when the front stem 232 of the fitting tip 23 is inserted into the second end section 221 of a light channel 220, the central axis 230 of the fitting tip 23 (and therefore the optical axis 100 of the inspector probe 10 fitted with the fitting tip 23) will be collinear with the central axis 2210 of the second end section 221. In either case, referring again to FIG. 6 and FIG. 7, the optical axis 100 of the inspector probe 10 fitted with the fitting tip 23 will extend through the light channel 220 and out of the template inserter 22, and if the guide 20 is coupled with the plug-type ruggedized connector 30, the optical axis 100 will be further aligned with the fiber optic endface 331 in view through the light channel 220.

Furthermore, the mid section 223 is disposed in relation to the first end section 222 and the second end section 221 such that an inner end surface 2221 is formed in the first end section 222 and an inner end surface 2211 is formed in the second end section 221. Therefore, when the front stem 232 of the fitting tip 23 is inserted into the first end section 222 of any of the light channels 220, the front end surface 231 of the fitting tip 23 will come in contact with and be stopped by the inner end surface 2221 of the first end section 222 of the light channel 220. Similarly, when the front stem 232 of the fitting tip 23 is inserted into the second end section 221 of any of the light channels 220, the front end surface 231 of the fitting tip 23 will come in contact with and be stopped by the inner end surface 2211 of the second end section 221 of the light channel 220.

As illustrated in FIG. 4 and FIG. 6, when a plug-type ruggedized connector 30 with PC endfaces 3311 are to be inspected, the template inserter 22 is connected to the frame 21 to form the guide 20, with the first end surface 228 facing the rear side of the frame 21 and with the first male screw thread 226 fastened to the female screw thread 212 of the frame 21. Then, the guide 20 is coupled with the plug-type ruggedized connector 30 as described above. Then, the front stem 232 of the fitting tip 23 already fitted on an inspector probe 10 is inserted into the first end section 222 of a selected one of the light channels 220. In this arrangement, the optical axis 100 of the inspector probe 10 will extend through the fitting tip 23 and the selected light channel 220 unobstructed, and continue on to intersect at a right angle with a center point on the PC endface 3311 that is in view through the selected light channel 220. In this arrangement, the central axis 2220 of the first end section 222 is collinear with the axis of the fiber optic terminus 330 with the PC endface 3311. Therefore, the PC endface 3311 so aligned may be inspected by the inspector probe 10. Once the inspection of the PC endface 3311 is completed, the fitting tip 23 may be withdrawn along with the inspector probe 10 and be inserted into the first end section 222 of another light channel 220 from the first end surface 228 to inspect the PC endface 3311 in view through that light channel 220. By repeating the steps, all the PC endfaces 3311 in the plug-type ruggedized connector 30 may be inspected one after another.

Similarly, as illustrated in FIG. 5 and FIG. 7, when a plug-type ruggedized connector 30 with APC endfaces 3312 are to be inspected, the template inserter 22 is connected to the frame 21 with the second end surface 227 facing the rear of the frame 21 and with the second male screw thread 225 fastened to the female screw thread 212 of the frame 21. Then, the guide 20 is coupled with the plug-type ruggedized connector 30 as described above. Then, the front stem 232 of the fitting tip 23 already fitted on an inspector probe 10 is inserted into the second end section 221 of a selected one of the light channels 220. In this arrangement, the optical axis 100 of the inspector probe 10 will extend at an angle α (relative to a normal of the second end surface 227) through the fitting tip 23 and the selected light channel 220 unobstructed, and continue on to intersect at a right angle with a center point on the APC endface 3312 that is in view through the selected light channel 220. Therefore, the APC endface 3312 so aligned may be inspected by the inspector probe 10. Once the inspection of the APC endface 3312 is completed, the fitting tip 23 may be withdrawn along with the inspector probe 10 and be inserted into the second end section 221 of another light channel 220 from the second end surface 227 of the template inserter 22 to inspect the APC endface 3312 in view through that light channel 220. By repeating the steps, all the APC endfaces 3312 in the plug-type ruggedized connector 30 may be inspected one after another.

Because the locating holes 229 of the template inserter 22 extend perpendicularly between the first end surface 228 and the second end surface 227 of the template inserter, when the guide pins 340 of the plug-type ruggedized connector 30 are inserted into the locating holes 229 of the template inserter 22, the axis of rotation 200 of the template inserter 22 will be parallel to the central axis of each of the fiber optic termini 330 in the plug-type ruggedized connector 30. In order to make sure that the optical axis 100 of the inspector probe 10 (connected as described above) intersect at a right angle with the PC endface 3311 to be inspected, the central axis 2220 of the first end section 222 of each light channel 220 must also be perpendicular to the PC endface 331 in view through the light channel 220. This is accomplished by making the inner cylindrical surface and therefore the central axis 2220 of the first end section 222 perpendicular to the first end surface 228 of the template inserter 22. On the other hand, in order to make sure that the optical axis 100 of the inspector probe 10 (connected as described above) intersect at a right angle with the APC endface 3312 to be inspected, the central axis of the second end section 221 of each light channel 220 must also be perpendicular to the APC endface 3312 in view through the light channel 220.

This is accomplished by making the inner cylindrical surface and therefore the central axis 2210 of the second end section 221 titled at an angle α from a normal of the second end section 221 of the template inserter 22, where a is the angle that the APC endface 3312 is tilted.

PC/APC Dual-Purpose Adapter for Circular Receptacle-Type Ruggedized Connector

Figure 8:
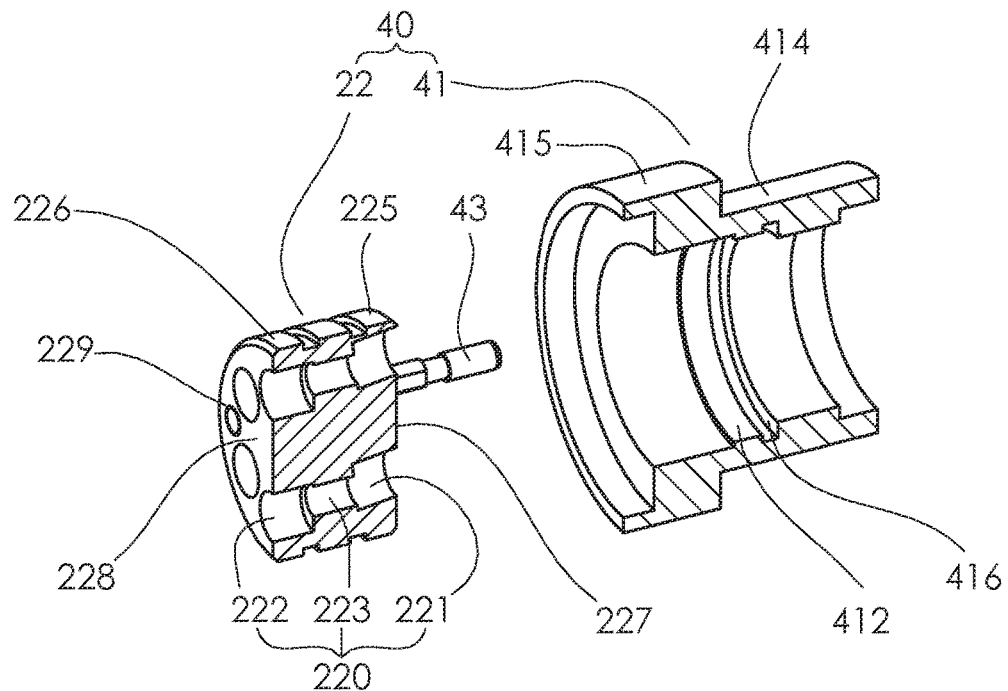
FIG. 8 is an exploded sectional view showing how the template inserter and the frame are coupled to form the guide of the present application for inspecting PC endfaces in a receptacle-type ruggedized connector.
Figure 9:
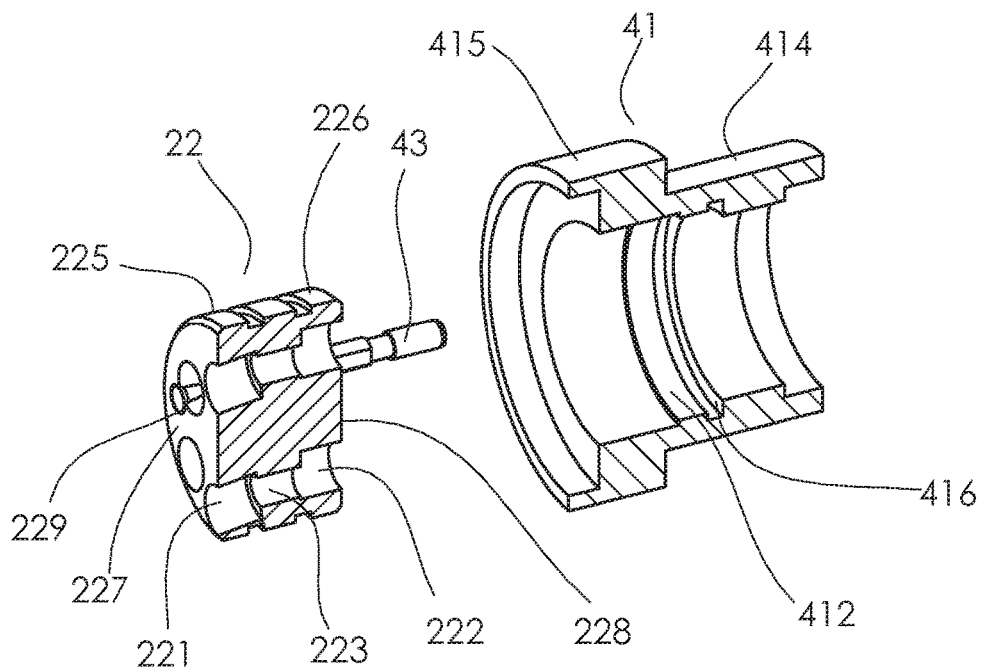
FIG. 9 is an exploded sectional view showing how the template inserter and the frame are coupled to form the guide of the present application for inspecting APC endfaces in a receptacle-type ruggedized connector.
Figure 10:
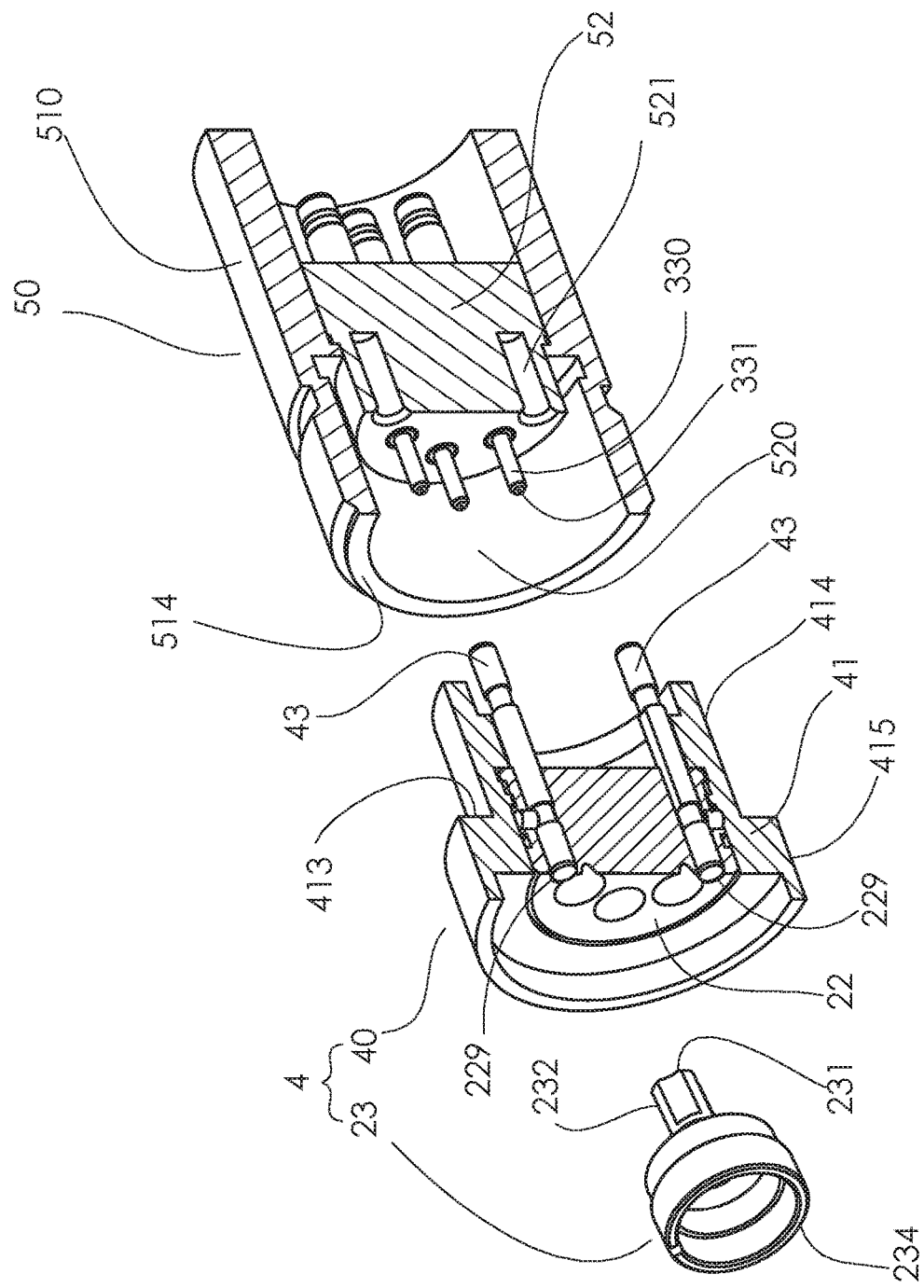
FIG. 10 is an exploded sectional view showing how the PC/APC adapter of the present application is coupled with a receptacle-type ruggedized connector for inspecting fiber optic endfaces enclosed therein.

The PC/APC dual-purpose adapter 2 described above may be further equipped or adapted for inspecting the circular receptacle-type ruggedized connector 50. Three exploded sectional views of the PC/APC dual-purpose adapter 4 for the receptacle-type ruggedized connector 50 are shown in FIG. 8, FIG. 9 and FIG. 10, respectively. The PC/APC dual-purpose adapter 4 includes a fitting tip 23, a guide 40 (including a template inserter 22 as described above and a frame 41), two guide pins 43 respectively movably disposed in the two locating holes 229 of the template inserter 22, and a mechanism for locking/unlocking the axial movement of the two guide pins 43 at two positions in the two locating holes 229. The description above for the PC/APC dual-purpose adapter 2 is generally applicable to the PC/APC dual-purpose adapter 4, except for the differences noted below.

The fitting tip 23 and the template inserter 22 of the guide 40 of the PC/APC dual-purpose adapter 4 for the receptacle-type ruggedized connector 50 have been described above for the PC/APC dual-purpose adapter 2.

Similarly, the frame 41 of the guide 40 of the PC/APC dual-purpose adapter 4 has a front annular connecting portion 414 adapted for coupling with a receptacle-type ruggedized connector 50, a rear annular portion 415, a through opening extending between the front annular connecting portion 414 and the rear annular portion 415, and an inner circular cylindrical surface, on which a female screw thread 412 is formed for fastening to either of the matching male screw threads 226/225 of the template inserter 22. The rear annular portion 415 has an outer diameter greater than that of the front annular connecting portion 414, thus forming an annular front surface 413, which will be stopped at the front end 514 of the receptacle-type ruggedized connector 50 when the front annular connecting portion 414 has been properly received in the open chamber 520 of the receptacle-type ruggedized connector 50. Just like the guide 20 for the plug-type ruggedized connector 30, the template inserter 22 may be connected to the frame 41 with either the first male screw thread 226 or the second male screw thread 225 fastened to the female screw thread 412 of the frame 41. FIG. 8 and FIG. 9 represent exploded sectional views of the guide 40, illustrating the template inserter 22 to be coupled with the frame 41 in two opposite directions. In FIG. 8, the template inserter 22 is oriented to couple with the frame 41 with the second end surface 227 facing the frame 41 and the second male screw thread 225 fastened to the female screw thread 412. In FIG. 9, the template inserter 22 is oriented to couple with the frame 41 with the first end surface 228 facing the frame 41 and the first male screw thread 226 fastened to the female screw thread 412.

Referring to FIG. 10, when the PC/APC dual-purpose adapter 4 is connected to the front end 514 of the receptacle-type ruggedized connector 50, the two guide pins 43 disposed in the two locating holes 229 of the template inserter 22 will be inserted into and fittingly held in the two locating holes 521 of the receptacle-type ruggedized connector 50, and the plurality of light channels 220 of the template inserter 22 will correspond in relative position to the plurality of fiber optic endfaces 331 of the receptacle-type ruggedized connector 50.

Figure 12:
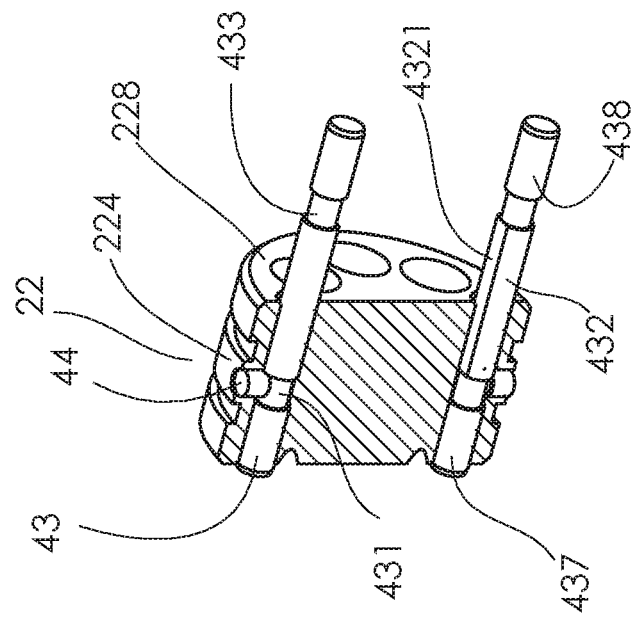
FIG. 12 is an exploded sectional view showing the structure of the guide pins, and their position and orientation when they are rotatable and may be locked/unlocked with respect to axial movement in the locating holes of the template inserter shown in FIG. 10.
Figure 11:
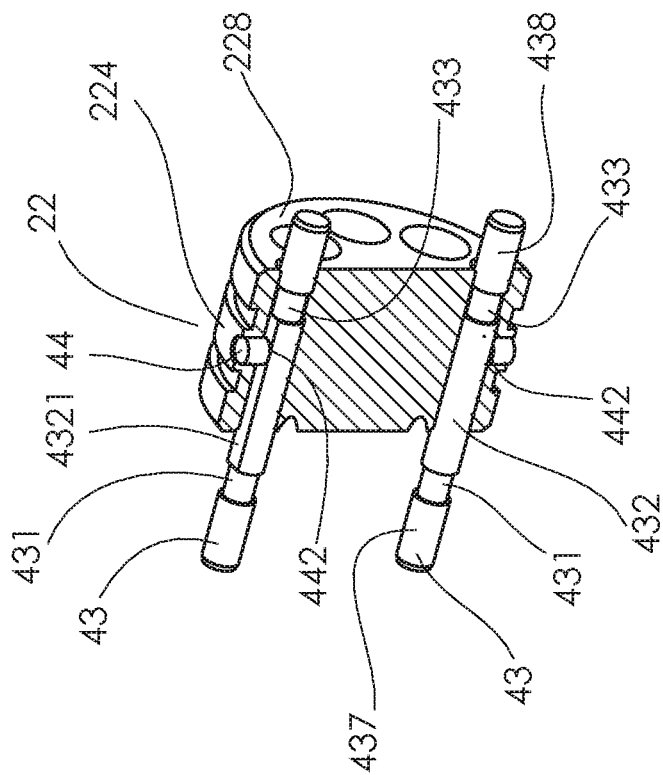
FIG. 11 is an exploded sectional view showing the structure of the guide pins, and their relative position and orientation when they are free to move axially in the locating holes of the template inserter shown in FIG. 10.

The mechanism for locking/unlocking the axial movement of the two guide pins 43 in the two locating holes 229 at two locking positions in the locating holes 229 consists in the outer contour of the guide pins 43 and a protrusion 44 disposed in each locating hole 229. As shown in FIG. 11 and FIG. 12, each guide pin 43 has a circular cylindrical first end portion 438, a circular cylindrical second end portion 437, a mid portion 432, and two circular cylindrical recessed portions 433, 431 between the mid portion 432 and the two end portions 438, 437, respectively. The two end portions 438, 437 and the two recessed portions 433, 431 are coaxial. The first end portion 438 and the second end portion 437 have the same diameter $r_1$, whereas the two recessed portions 433, 431 have the same diameter $r_2$, which is smaller than $r_1$. The mid portion 432 is a circular cylindrical portion of a diameter $r_1$ with a cylindrical segment cut off by a plane at a distance $r_2$ from and parallel to the axis of the circular cylindrical portion, and the corresponding circular cylindrical portion would be coaxial with the two end portions 438, 437 and the two recessed portions 433, 431. In other words, the mid portion 432 has a cross section that is a circle of a diameter $r_1$ with a circular segment cut off along a chord of the circle, wherein the chord is at a distance $r_2$ from the center of the circle. Therefore, a rectangular flat surface 4321 is formed between the two recessed portions 433, 431. At the junction between the recessed portions 433, 431 and the mid portion 432, the flat surface 4321 of the mid portion 432 is tangential to the recessed portions 433, 431.

Moreover, as shown in FIG. 11 and FIG. 12, the mechanism referenced above for locking/unlocking the axial movement of the guide pins 43 in the locating holes 229 further includes a protrusion 44 having a flat end surface 442 transversely (in the radial direction) extending from the inner surface of each of the locating holes 229, or through the outer surface 224 of the template inserter 22 into each of the locating holes 229. The flat end surface 442 of each protrusion 44 should be located at a distance of about $r_2$ from the axis of the respective locating hole 229. Preferably, the protrusion 44 for each locating hole 229 is disposed midway between the first end surface 228 and the second end surface 227 of the template inserter 22, and is inserted or screwed through the outer surface 224 into the locating hole 229 after a respective guide pin 43 is inserted into the locating hole 229. As shown in FIG. 11, when the guide pin 43 is turned to have the flat surface 4321 of the mid portion 432 face the flat end surface 442 of the protrusion 44, the flat end surface 442 will nearly contact the flat surface 4321. At this time, the guide pin 43 is free to move in an axial direction inside the locating hole 229, while letting the flat end surface 442 of the protrusion 44 to glide over the flat surface 4321 of the mid portion 432. When either recessed portion 433/431 of each guide pin 43 is aligned with the protrusion 44 in the radial direction, as shown in FIG. 12, the guide pin 43 is free to turn in the respective locating hole 229. Once the flat surface 4321 no longer faces the flat end surface 442 of the protrusion 44, the guide pin 43 will be locked from axial movement.

Therefore, the guide pins 43 may be locked at two locking positions. At the first locking position, the recessed portion 433 of each guide pin 43 is aligned with the flat end surface 442 of the protrusion 44, and the guide pin 43 is locked in place with the second end portion 437 protruding out of the second end surface 227 of the template inserter 22 for mating with a locating hole 521 of the receptacle-type ruggedized connector 50. The guide pin 43 in FIG. 8 is locked at this locking position. On the other hand, at the second locking position, as illustrated in FIG. 12, the recessed portion 431 of each guide pin 43 is aligned with the flat end surface 442 of the protrusion 44, and the guide pins 43 is locked in place with the first end portion 438 protruding out of the first end surface 228 of the template inserter 22 for mating with a locating holes 521 of the receptacle-type ruggedized connector 50. The guide pin 43 in FIG. 9 is locked at this locking position.

Therefore, when the PC/APC dual-purpose adapter 4 is hooked up with a receptacle-type ruggedized connector 50 to inspect PC fiber optic endfaces 3311 enclosed therein, each of the guide pins 43 is moved axially to the first locking position to be locked in place as described above; when the template inserter 22 is fastened to the frame 41 with the second end surface 227 facing the frame 41, the front annular connecting portion 414 of the frame 41 is mated with the receptacle-type ruggedized connector 50 with the second end portion 437 of each of the guide pins 43 inserted into a respective locating hole 521 of the receptacle-type ruggedized connector 50, thus bringing the light channels 220 in the template inserter 22 to correspond in relative position to the PC endfaces 3311 in the receptacle-type ruggedized connector 50. The PC endfaces 3311 may then be inspected by an inspector probe 10 fitted with the fitting tip 23, in the same way as described above for the PC/APC dual-purpose adapter 2.

Alternatively, when inspecting APC fiber optic connector endfaces 3312 in a receptacle-type fiber optic connector 50, each of the guide pins 43 is moved axially to the second locking position to be locked in place as described above; when the template inserter 22 is coupled with the frame 41 with the first end surface 228 facing the frame 41, the front annular connecting portion 414 of the frame 41 is mated with the receptacle-type ruggedized connector 50 with the first end portion 438 of each of the guide pins 43 inserted into a respective locating holes 521 of the receptacle-type ruggedized connector 50, thus bringing the light channels 220 in the template inserter 22 to correspond in relative position to the APC endfaces 3312 in the receptacle-type ruggedized connector 50. The APC endfaces 3312 may then be inspected by an inspector probe 10 fitted with the fitting tip 23, as described above for the PC/APC dual-purpose adapter 2.

In this embodiment, the template inserter 22 is fastened into the female screw thread 412 of frame 41 from the rear annular portion 415 for the two to be fastened until the template inserter 22 is stopped at an inner annular surface 416 of the frame 41. Therefore, as shown in FIG. 8 and FIG. 9, it is the male screw thread toward the front side of the frame 41 (i.e. the second male screw thread 225 in FIG. 8 or the first male screw thread 226 in FIG. 9) that is to be fastened to the female screw thread 412 of the frame 41. However, the two may be designed such that the template inserter 22 is inserted into the frame 41 from the front annular connecting portion 414. In that case, it is the male screw thread toward the rear side of the frame 41 that is to be fastened to the female screw thread 412 of the frame 41. For this reason, the term "first/second male screw thread" in the attached claims shall not be limited to meaning "the male screw thread more adjacent to the first/second end surface".

Structure of Fitting Tip for Ruggedized Connectors

Figure 13:
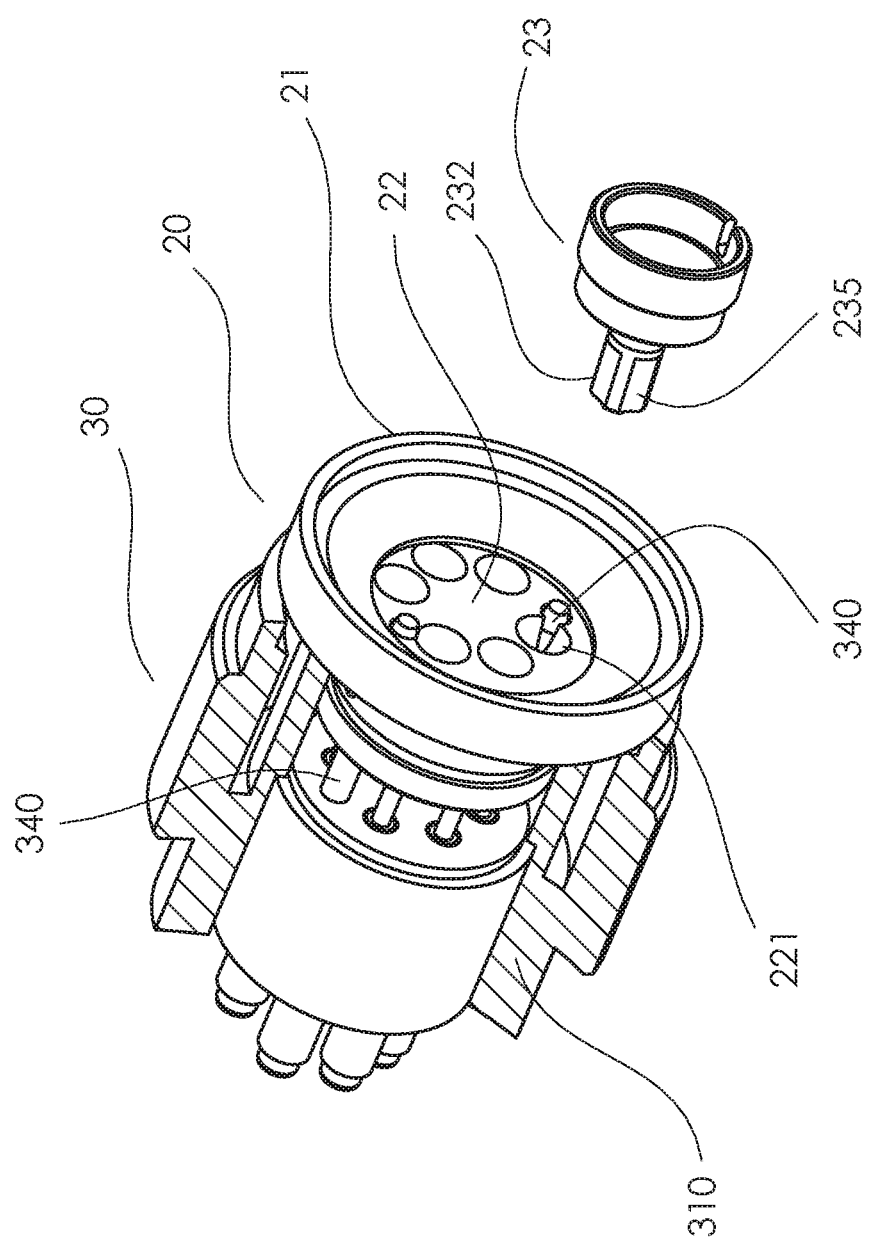
FIG. 13 shows the each locating hole crisscrossing with a light channel on one side of the template inserter of the PC/APC dual-purpose adapter when connected to a ruggedized connector.

As shown in FIG. 13, because the second end section 221 of the light channels 220 is angled, each locating hole 229 will likely crisscross with the second end section 221 of one of the light channels. As a result, the front end of a conventional fitting tip 73 will be prevented by a guide pin 340 (from the plug-type ruggedized connector 30) or 43 (as a component of the plug 40) from inserting into the second end section 221. To resolve this problem, the front stem 232 of the fitting tip 23 is shaped to have four grooves 235 evenly distributed around its outer surface, as shown in FIG. 14 and FIG. 15. FIG. 15 shows the cross section of the front stem 232. This design of the fitting tip 23 not only retains sufficient overall strength of the front stem 232, but also sufficient contact area between the front end surface 231 of the fitting tip 23 and the inner end surface 2211/2221 (see FIG. 6 and FIG. 7) in the light channel.

The invention is not to be limited to the exact structure and features shown in the accompanying drawings or described in the specification as various changes in the details of construction may be made without departing from the spirit of the invention.

What is claimed is:
1. An PC/APC dual-purpose adapter for inspecting a circular plug-type ruggedized fiber optic connector using an inspector probe, the PC/APC dual-purpose adapter comprising:
   a frame;
   a template inserter; and
   a fitting tip,
   wherein the template inserter comprises
      a first end surface,
      a second end surface parallel to the first end surface,
      a cylindrical outer surface between the first end surface and the second end surface,
      a plurality of internal light channels extending between the first end surface and the second end surface,
      two locating holes perpendicularly extending between the first end surface and the second end surface, and
      a first male screw thread and a second male screw thread formed on the outer surface,
      wherein the plurality of light channels respectively correspond to a plurality of fiber optic endfaces in the plug-type ruggedized fiber optic connector, and
      each of the internal light channels comprises
         a cylindrical first end section extending inwards from the first end surface,
         a cylindrical second end section extending inwards from the second end surface, and
         a mid section between the first end section and the second end section,
         wherein the first end section has an axis perpendicular to the first end surface, and
         the second end section has an axis intersecting the second end surface at an angle α from a normal of the second end surface, wherein α is a tilted angle of APC endfaces of the plug-type ruggedized fiber optic connector;
   the frame has a front annular connecting portion for coupling with the plug-type ruggedized fiber optic connector, and an internal cylindrical surface having thereon a female screw thread matching the first and the second male screw threads of the template inserter; and
   the fitting tip has a hollow cylindrical front stem fittingly insertable into the first end section or the second end section of each of the internal light channels, and a rear portion connectable to an inspector probe such that an axis of the front stem is aligned with an optical axis of the inspector probe,
   wherein the template inserter may be coupled with the frame by either (1) fastening the first male screw thread to the female screw thread of the frame; or (2) fastening the second male screw thread to the female screw thread of the frame, whereby (1) when inspecting the plug-type ruggedized fiber optic connector with PC endfaces, the template inserter is coupled with the frame with the first male screw thread fastened to the female screw thread of the frame, the fitting tip is inserted into the first end section of a selected internal light channel, the front annular connecting portion of the frame is coupled with the plug-type ruggedized fiber optic connector, and two guide pins of the plug-type ruggedized fiber optic connector are respectively inserted into the two locating holes of the template inserter, then a PC fiber optic endface of the plug-type ruggedized fiber optic connector will be in view through the selected internal light channel for inspection by the inspector probe connected to the fitting tip; and (2) when inspecting the plug-type ruggedized fiber optic connector with APC endfaces, the template inserter is coupled with the frame with the second male screw thread fastened to the female screw thread of the frame, the fitting tip is inserted into the second end section of a selected internal light channel, the front annular connecting portion of the frame is coupled with the plug-type ruggedized fiber optic connector, and two guide pins of the plug-type ruggedized fiber optic connector are respectively inserted into the two locating holes of the template inserter, then an APC fiber optic endface of the plug-type ruggedized fiber optic connector will be in view through the selected internal light channel for inspection by the inspector probe connected to the fitting tip.

2. The PC/APC dual-purpose adapter of claim 1, wherein the $\alpha$ is about 8°.

3. The PC/APC dual-purpose adapter of claim 1, wherein the front stem of the fitting tip is shaped to have a plurality of grooves evenly distributed around an outer surface thereof.

4. The PC/APC dual-purpose adapter of claim 3, wherein the plurality of grooves on the front stem of the fitting tip corresponds to four grooves.

5. The PC/APC dual-purpose adapter of claim 1, wherein the frame further comprises a rear annular portion having an outer diameter greater than that of the front annular connecting portion, thus forming an annular front surface thereof such that when the frame is coupled with the plug-type ruggedized fiber optic connector, the annular front surface of the rear annular portion is stopped against a front end of the plug-type ruggedized fiber optic connector.

6. The PC/APC dual-purpose adapter of claim 5, wherein the rear annular portion of the frame has an inner diameter proportionally increasing in the direction towards a rear end of the frame, thus forming an expanding rear-facing opening.

7. An PC/APC dual-purpose adapter for inspecting a circular receptacle-type ruggedized fiber optic connector by an inspector probe, the PC/APC dual-purpose adapter comprising:
a frame;
a template inserter;
two guide pins; and
a fitting tip,
wherein the template inserter comprises
a first end surface,
a second end surface parallel to the first end surface,
a cylindrical outer surface between the first end surface and the second end surface,
a plurality of internal light channels extending between the first end surface and the second end surface, two locating holes perpendicularly extending between the first end surface and the second end surface, and
a first male screw thread and a second male screw thread formed on the outer surface,
wherein the plurality of light channels respectively correspond to a plurality of fiber optic endfaces in the receptacle-type ruggedized fiber optic connector, and
each of the internal light channels comprises
a cylindrical first end section extending inwards from the first end surface,
a cylindrical second end section extending inwards from the second end surface, and
a mid section between the first end section and the second end section,
wherein the first end section has an axis perpendicular to the first end surface,
the second end section has an axis intersecting the second end surface at an angle $\alpha$ from a normal of the second end surface, where $\alpha$ is a tilted angle of APC endfaces of the receptacle-type ruggedized fiber optic connector;
the two guide pins are respectively received in the two locating holes of the template inserter, wherein each of the guide pins is axially movable in the respective locating hole, and may be locked or unlocked with respect to axial movement at a first locking position, wherein $\alpha$ second end portion of the guide pin protrudes out of the second end surface of the template inserter; or at a second locking position, wherein a first end portion of the guide pin protrudes out of the first end surface of the template inserter;
the frame has a front annular connecting portion for coupling with the receptacle-type ruggedized fiber optic connector, and an internal cylindrical surface having thereon a female screw thread matching the first and the second male screw threads of the template inserter; and
the fitting tip has a hollow cylindrical front stem fittingly insertable into the first end section or the second end section of each of the internal light channels, and a rear portion connectable to an inspector probe such that an axis of the front stem is aligned with an optical axis of the inspector probe,
wherein the template inserter may be coupled with the frame by either (1) fastening the first male screw thread to the female screw thread of the frame; or (2) fastening the second male screw thread to the female screw thread of the frame,
whereby (1) when inspecting the receptacle-type ruggedized fiber optic connector with PC endfaces, the template inserter is coupled with the frame with the first male screw thread fastened to the female screw thread of the frame, the fitting tip is inserted into the first end section of a selected internal light channel, the front annular connecting portion of the frame is coupled with the receptacle-type ruggedized fiber optic connector, and the two guide pins are each locked at the first locking position with the second end portions of the guide pins respectively inserted into two locating holes of the receptacle-type ruggedized fiber optic connector, then a PC fiber optic endface of the receptacle-type ruggedized fiber optic connector will be in view through the selected light channel for inspection by the inspector probe connected to the fitting tip; and (2) when inspecting the receptacle-type ruggedized fiber optic connector with APC endfaces, the template inserter is coupled with the frame with the second male screw thread fastened to the female screw thread of the frame, the fitting tip is inserted into the second end section of a selected internal light channel, the front annular connecting portion of the frame is coupled with the receptacle-type ruggedized fiber optic connector, and the two guide pins are each locked at the second locking position with the first end portions of the two guide pins respectively inserted into the two locating holes of the receptacle-type ruggedized fiber optic connector, then an APC fiber optic endface of the receptacle-type ruggedized fiber optic connector will be in view through the selected light channel for inspection by the inspector probe connected to the fitting tip.

8. The PC/APC dual-purpose adapter of claim 7, wherein $\alpha$ is about 8°.

9. The PC/APC dual-purpose adapter of claim 7, wherein the front stem of the fitting tip is shaped to have a plurality of grooves evenly distributed around an outer surface thereof.

10. The PC/APC dual-purpose adapter of claim 9, wherein the plurality of grooves on the front stem of the fitting tip corresponds to four grooves.

11. The PC/APC dual-purpose adapter of claim 7, wherein the frame further comprises a rear annular portion having an outer diameter greater than that of the front annular connecting portion, thus forming an annular front surface thereof such that when the frame is coupled with the receptacle-type ruggedized fiber optic connector, the annular front surface of the rear annular portion is stopped against a front end of the receptacle-type ruggedized fiber optic connector.

12. The PC/APC dual-purpose adapter of claim 7, wherein
each of the two guide pins further comprises a mid portion, a first recessed portion between the first end portion and the mid portion, and a second recessed portion between the second end portion and the mid portion;
the first end portion and the second end portion each have a circular cross section of radius $r_1$, which is essentially the same as the radius of the locating holes of the template inserter;
the first recessed portion and the second recessed portion each have a circular cross section of radius $r_2$, wherein $r_2 < r_1$;
the mid portion has a cross section that is a circle of radius $r_1$ with a segment of the circle removed along a chord at a distance $r_2$ from the center of the circle, such that a flat surface subsuming the chord is formed between the first recessed portion and the second recessed portion;
a protrusion extends radially from an inner surface of each of the locating holes, wherein the protrusion has an end surface located at a distance of about $r_2$ from the axis of the locating hole,
wherein when the protrusion in each of locating holes is radially aligned with the first recessed portion of the guide pin received in the locating hole, the guide pin is at the first locking position; and when the protrusion in each of the locating holes is radially aligned with the second recessed portion of the guide pin received in the locating hole, the guide pin is at the second locking position;
wherein when each of the guide pins is at the first or the second locking position, the guide pin is rotatable in the locating hole, and is locked with respect to axial movement unless the protrusion is axially aligned with the flat surface of the mid section of the guide pin.

13. The PC/APC dual-purpose adapter of claim 12, wherein the protrusion in each of the locating holes is part of a pin disposed through the outer surface of the template inserter.

* * * * *